United States Patent [19]

Bogan et al.

[11] Patent Number: 4,806,625

[45] Date of Patent: Feb. 21, 1989

[54] FLAME RESISTANT POLYAROMATIC CYANATE RESINS WITH IMPROVED THERMAL STABILITY

[75] Inventors: Gary W. Bogan; Georgia A. Monnerat, both of Lake Jackson, Tex.

[73] Assignee: The Dow Chemical Company, Midland, Mich.

[21] Appl. No.: 142,983

[22] Filed: Jan. 12, 1988

[51] Int. Cl.$^4$ .............................................. C08G 73/00
[52] U.S. Cl. ................................ 528/422; 528/392; 528/425
[58] Field of Search ...................... 528/422, 392, 425

[56] References Cited

U.S. PATENT DOCUMENTS 4,097,455  6/1978  Burkhardt et al. .................... 528/67
4,751,323  6/1988  Woo et al. ........................... 528/422

Primary Examiner—Harold D. Anderson
Assistant Examiner—T. Mason

[57] ABSTRACT

Halogen-containing hydrocarbon phenol cyanate resins are prepared by reacting the product resulting from reacting a hydrocarbon phenol resin with a metahalogenated hydroxymethyl phenol with a cyanogen halide.

56 Claims, No Drawings

FLAME RESISTANT POLYAROMATIC CYANATE RESINS WITH IMPROVED THERMAL STABILITY

FIELD OF THE INVENTION

The present invention concerns polyaromatic cyanate resins which are flame resistant and which exhibit improved thermal stability.

BACKGROUND OF THE INVENTION

Aromatic cyanate esters derived from bisphenol A exhibit high glass transition temperatures, but suffer from high dielectric constants and vulnerability to moisture attack. Aromatic cyanate esters derived from hydrocarbon (dicyclopentadienyl) phenols offer improved moisture resistance and electrical properties, but lack flame retardancy required in many electrical laminate applications. It would therefore be desirable to have hydrocarbon phenol cyanate resins which exhibit some flame retardancy.

SUMMARY OF THE INVENTION

One aspect of the present invention pertains to halogen-containing hydrocarbon phenol cyanate resins represented by the following formula I

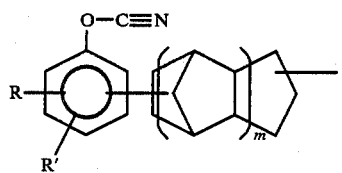

FORMULA I

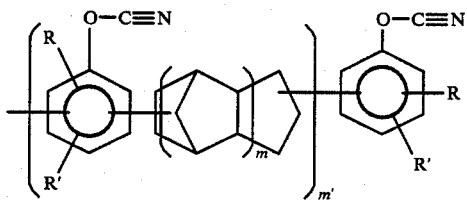

wherein each R is independently hydrogen or an alkyl group having from 1 to about 10 carbon atoms; each m independently has a value from 1 to about 6; each m' has an average value from zero to about 4; each R' is independently hydrogen or a group represented by the following formula II;

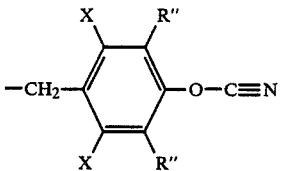

FORMULA II wherein each R" is independently an alkyl group having from 1 to about 4 carbon atoms; each X is a halogen; with the proviso that at least one R' group is a group represented by the formula II.

Another aspect of the present invention pertains to a mixture comprising (A) at least one hydrocarbon phenol cyanate resin represented by the following formula I

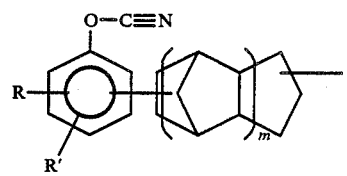

FORMULA I

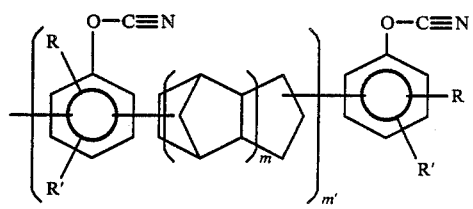

wherein each R is independently hydrogen or an alkyl group having from 1 to about 10 carbon atoms; each m independently has a value from 1 to about 6; m' has an average value from zero to about 4; each R' is independently hydrogen or a group represented by the following formula II

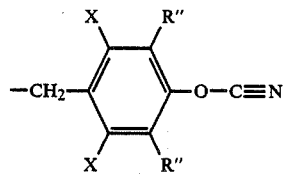

FORMULA II wherein each R" is independently an alkyl group having from 1 to about 4 carbon atoms; each X is a halogen; with the proviso that at least one R' group is a group represented by formula II; and (B) at least one halogen-free hydrocarbon phenol cyanate resin represented by the following formula III

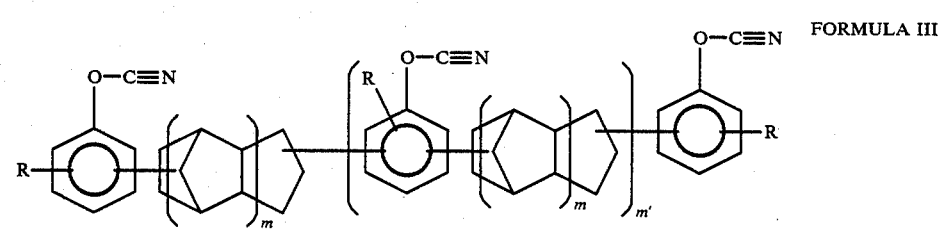

FORMULA III wherein each R is independently hydrogen or an alkyl group having from 1 to about 10 carbon atoms; each m independently has a value from 1 to about 6; m' has an average value from zero to about 4;

wherein component (A) is present in an amount of from about 1 to about 99 percent by weight and component (B) is present in an amount of from about 99 to about 1 percent by weight based upon the combined weight of components (A) and (B).

Another aspect of the present invention pertains to a curable composition comprising a hydrocarbon phenol cyanate resin represented by formula I or a mixture of hydrocarbon phenol cyanate resins represented by formulas I and III with a curing quantity of a suitable curing agent.

A further aspect of the present invention pertains to the product resulting from curing the aforementioned curable composition.

DETAILED DESCRIPTION OF THE INVENTION

The halogen-containing hydrocarbon phenol cyanate resins of the present invention can be prepared by reacting hydrocarbon phenol resin with a hydroxymethyl or halomethyl metahalogenated phenol. This reaction is suitably conducted at a temperature of from about 30° C. to about 180° C., more suitably from about 50° C. to about 160° C., most suitably from about 80° C. to about 150° C. for a time sufficient to complete the reaction, usually from about 1 to about 30, more usually from about 2 to about 15, most usually, from about 3 to about 10, hours. The higher the temperature, the shorter the reaction time; likewise, the lower the temperature, the longer the reaction time. If desired, the reaction can be conducted in the presence of solvents such as, for example, aromatic hydrocarbons, aromatic or aliphatic ketones, halogenated hydrocarbons, aliphatic hydrocarbons, combinations thereof and the like. Particularly suitable such solvents include, for example, toluene, methyl isobutyl, ethylene dichloride, octane, combinations thereof and the like.

Hydrocarbon phenol resins can be prepared by reacting dicyclopentadiene or oligomers thereof with a aromatic hydroxyl-containing compound. This reaction can suitably be conducted at temperatures of from about −20° C. to about 165° C., more suitably from about 50° C. to about 100° C., most suitably from about 60° C. to about 90° C. for a time sufficient to complete the addition of the dicyclopentadiene to the reaction mixture, usually from about 0.25 to about 8, more usually, from about 0.5 to about 4, most usually, from about 1 to about 2, hours. This is usually followed by a reaction digestion period which can be suitably conducted at temperatures of from about 140° C. to about 200° C., more suitably from about 145° C. to about 175° C. and most suitably from about 145° C. to about 155° C. for a time sufficient to complete the reaction, usually from about 0.5 to about 6, more usually from about 1 to about 5, most usually from about 2 to about 4 hours. The higher the temperature, the shorter the reaction time; likewise, the lower the temperature, the longer the reaction time. If desired, the reaction can be conducted in the presence of solvents such as, for example, aprotic solvents such as aliphatic and aromatic hydrocarbons, chlorinated hydrocarbons, combinations thereof and the like. Particularly suiable such solvents include, for example, toluene, methylene chloride, carbon tetrachloride, combinations thereof and the like.

Metahalogenated phenols can be prepared by reacting bromine or other reactive halogen with mesitol (2,4,6-trimethyl phenol) or other suitable phenol. The resulting halomethyl metahalogenated phenol can then be reacted with the hydrocarbon phenol resins or, optionally, hydrolyzed to the corresponding hydroxymethyl metahalogenated phenol which can then be reacted with the hydrocarbon phenol resins. The reaction of halogen with substituted phenol can suitably be conducted in an inert solvent at temperatures of from about 30° C. to about 100° C., more suitably from about 40° C. to about 90° C., and most suitably from about 50° C. to about 80° C., depending upon the reflux temperature of the reaction solvent chosen. Suitable solvents include, for example, ketones, alcohols, halogenated hydrocarbons, aliphatic or aromatic hydrocarbons, esters, combinations thereof and the like. Particularly suitable solvents include, for example, methylene chloride, carbon tetrachloride, dichloromethane, cyclohexane, combinations thereof and the like.

Hydrolysis of the halomethyl metahalogenated phenol to the corresponding hydroxymethyl metahalogenated phenol can be accomplished by reacting the halomethyl metahalogenated phenol with water in the presence of a suitable inert solvent. This reaction can suitably be conducted at temperatures of from about 30° C. to about 100° C., more suitably from about 40° C. to about 90° C., and most suitably from about 50° C. to about 80° C., depending upon the reflux temperature of the reaction solvent chosen. Suitable solvents include those which are completely miscible with water or have a high water solubility and which are not reactive toward ether formation. Particularly suitable solvents include, for example, dimethyl formamide, dimethyl acetamide, dimethyl sulfoxide, 2-methoxyethyl acetate, ethylene glycol dimethyl ether, dioxane, N-methylpyrrolidone, tetrahydrofuran, acetone, combinations thereof and the like.

The hydorcarbon phenol cyanate resins can be prepared by reacting the product resulting from reacting a hydrocarbon phenol resin with a metahalogenated hydroxymethyl phenol with a cyanogen halide, such as, for example cyanogen chloride or cyanogen bromide or a combination thereof in the presence of a base such as triethyl amine or other trialkyl amine. Such suitable basic catalysts are disclosed in British Pat. No. 1,007,790 which is incorporated herein by reference. This reaction can suitably be conducted at temperatures of from about −40° C. to about 65° C., more suitable from about −20° C. to about 10° C., most suitably from about −20° C. to about −15° C. for a time sufficient to complete the reaction, usually from about 0.5 to about 8, more usually from about 1 to about 6, most usually, from about 1.5 to about 3, hours. The higher the temperature, the shorter the reaction time; likewise, the lower the temperature, the longer the reaction time. If desired, the reaction can be conducted in the presence of solvents such as, for example, aliphatic ketones, secondary or tertiary alcohols, chlorinated aliphatic hydrocarbons, chlorinated aromatic hydrocarbons, aliphatic hydrocarbons, aromatic hydrocarbons, combinations thereof and the like. Particularly suitable such solvents include, for example, methylene chloride, acetone, isopropyl alcohol, combinations thereof and the like.

Suitable hydrocarbon phenol resins which can be employed herein include, for example, those represented by the following formula IV

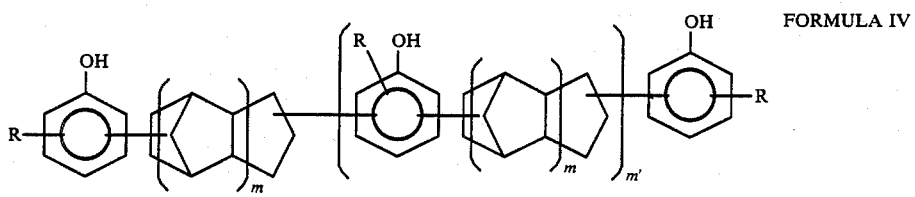

FORMULA IV wherein each R is independently hydrogen or an alkyl group having suitably from 1 to about 10, more suitably from 1 to about 6, most suitably from 1 to about 2, carbon atoms; each m independently has a value suitably from 1 to about 6, more suitably from 1 to about 3, most suitably from 1 to about 2; m' has an average value suitably from zero to about 4, more suitably from zero to about 2, most suitably from zero to about 1. Particularly suitable hydrocarbon phenol resins include those disclosed by Donald L. Nelson in U.S. Pat. No. 4,390,680; by Bebhart et al in U.S. Pat. No. 3,557,239; and by Vegter et al. in U.S. Pat. No. 3,536,734 all of which are incorporated herein by reference.

Suitable hydroxymethyl or halomethyl metahalogenated phenols which can be employed herein include those represented by the following formula V

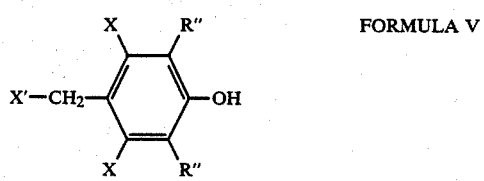

FORMULA V wherein each R' is independently an alkyl group having suitably from 1 to about 4, more suitably from 1 to about 2, most suitably 1, carbon atom(s); each X is a halogen, preferably chlorine or bromine, most preferably bromine; and X' is a hydroxyl group, chlorine or bromine. Particularly suitable hydroxymethyl or halomethyl matahalogenated phenols include, for example, 3,5-dibromo-4-hydroxymethyl-2,6-dimethyl phenol, 3,5-dibromo-4-hydroxymethyl-2,6-diethyl phenol, 3,5-dibromo-4-chloromethyl-2,6-dimethyl phenol, 3,5-dibromo-4-chloromethyl-2,6-diethyl phenol, 3,5-dibromo-4-bromomethyl-2,6-dimethyl phenol, 3,5-dibromo-4-bromomethyl-2,6-diethyl phenol, 3,5-dichloro-4-hydroxymethyl-2,6-dimethyl phenol, 3,5-dichloro-4-hydroxymethyl-2,6-diethyl phenol, 3,5-dichloro-4-chloromethyl-2,6-dimethyl phenol, 3,5-dichloro-4-chloromethyl-2,6-diethyl phenol, 3,5-dichloro-4-bromomethyl-2,6-dimethyl phenol, 3,5-dichloro-4-bromomethyl-2,6-diethyl phenol, combinations thereof and the like.

The mixture of hydrocarbon phenol cyanate resins represented by formulas I and III can be employed in quantities which provide suitably from about 1 to about 99, more suitably from about 10 to about 90, most suitably from about 15 to about 85, percent of the resin represented by formula I and from about 99 to about 1, more suitably from about 90 to about 10, most suitably from about 85 to about 15, percent of the resin represented by formula III based upon the combined weight of the resins represented by formulas I and III.

Suitable curing agents or catalysts which can be employed herein include acids, bases, salts, nitrogen and phosphorus compounds, for example, Lewis acids such as $AlCl_3$, $BF_3$, $FeCl_3$, $TiCl_4$, $ZnCl_2$, $SnCl_4$; proton acids such as HCl, $H_3PO_4$; aromatic hydroxyl containing compounds such as phenol, alkyl phenols, p-nitrophenol, pyrocatechol, dihydroxy naphthalene; sodium hydroxide, sodium methylate, sodium phenolate, trimethylamine, triethylamine, tributylamine, diazobicyclo-(2,2,2)-octane, quinoline, isoquinoline, tetrahydroisoquinoline, tetraethyl ammonium chloride, pyridine-N-oxide, tributylphosphine, phospholine-$66^3$-1-oxa-1-phenyl; transition metal salts, carboxylates, and complexes such as zinc octoate, tin octoate, zinc naphthenate, cobalt salts of $C_{6-20}$ carboxylic acids and mixtures thereof. Preferable curing agents or catalysts are the cobalt salts of $C_{6-20}$ carboxylic acids, with cobalt naphthenate, and cobalt octoate being most preferred, or cobalt acetylacetonate.

The curing agent or catalyst is employed in any quantity which can cure the hydrocarbon polyphenyl cyanate resins. Suitable amounts of curing agents or catalysts include, from about 0.001 to about 10, more suitably from about 0.02 to about 0.5, most suitably from about 0.025 to about 0.2, percent by weight of the curing agent or catalyst based upon the weight of the hydrocarbon polyphenyl cyanate resin(s) to be cured. The level of curing agent or catalyst desired is dependent on the choice of curing agent and the desired cure time.

If desired, accelerators for the curing agent can be employed such as, for example, alkyl phenols such as octyl, phenol, nonyl phenol, combinations thereof and the like.

The polyfunctional aromatic polycyanates can be combined in a solid or molten state, or optionally in solution with the powder-form or fibrous fillers, dyes, pigments, or reinforcing materials. For example, it is possible to impregnate powder-form or fibrous fillers or reinforcing materials such as quartz sand or glass cloths, with the aromatic cyanates, optionally in solution. Examples of the solvents which can be used for this purpose and which, generally, have to be removed again afterwards, are inert solvents such as methylene chloride, acetone, methyl ethyl ketone, xylene, ethyl acetate, benzene, toluene, tetrahydrofuran, chlorobenzene, dibutyl ether, dimethyl formamide, tetramethylene sulfone, combinations thereof and the like.

Suitable fillers and reinforcing materials are, generally, in powder and/or fibrous form, for example, of the type commonly used in the production of moldings based on unsaturated polyester resins or epoxy resins. Examples of products such as these are, primarily, granular fillers such as quartz powder, ground shale, powdered corundum, chalk, iron powder, aluminum powder, sand, gravel and other fillers of this kind, also inorganic or organic fibers, more especially glass fibers, rayon fibers, nylon fibers, graphite fibers or combinations thereof in the usual textile forms of fibers, filaments, rovings, yarns, nonwovens, mats and cloths and the like. It is also possible to use corresponding textile structures of organic, preferably synthetic, fibers (polyamides, polyesters) as well as textile structures formed from quartz, carbon, and metal fibers, and the like as well as monocrystals (whiskers).

These additives are provided in functionally equivalent amounts, eg, the pigments and/or dyes are added in quantities which will provide the composition with the desired color; however, they are suitably employed in amounts similar to those employed with epoxy resins and polyester resins, eg, suitably in amounts of from about 5 to about 90, more suitably from about 10 to about 80, most suitably from about 20 to about 75 percent by weight based upon the combined weight of the pigment and/or dyes and the polyfunctional aromatic cyanate.

The fillers can be employed in amounts similar to those employed with epoxy resins and polyester resins, suitably from about 5 to about 90, more suitably from about 10 to about 80, most suitably from about 20 to about 75 percent by weight based upon the combined weight of the filler and the polyfunctional aromatic cyanate.

The following examples are illustrative of the invention but are not to be construed as to limiting the scope thereof.

EXAMPLE 1

A. Preparation of Dicyclopentadiene Phenol Resin

Molten phenol (1333 lbs., 604.65 kg, 6425.6 OH equiv.) is agitated in a stainless steel reactor while boron trifluoride gas (3 lbs., 1.36 kg) is introduced. Dicyclopentadiene (187 lbs., 84.8 kg, 641.4 equiv.) is added slowly over a period of about 111 minutes, while maintaining the reaction temperature at about 68° C.–85° C. The temperature of the reaction mixture is then increased to 145° C. for three hours. Unreacted phenol is removed by vacuum distillation at temperatures from 145° C. to 180° C. and pressures from 1–11 psia (6.9–75.8 kPa). The entire process requires 806 minutes, during which time a steam distillation is employed for about 45 minutes. The product which is recovered has an average functionality of about 2.18 and a phenolic equivalent weight of about 164.

B. Preparation of Metahalogenated Phenol 3,5-dibromo-2,6-dimethyl-4-hydroxymethyl phenol is prepared in the following manner.

(1) Preparation of 4-bromomethyl-3,5-dibromo-2,6-dimethyl phenol (tribromomesitol)

A 136.2 gram portion of 2,4,6-trimethyl phenol (1 mole) is dissolved in 2 liters of carbon tetrachloride. Using a water bath for cooling, 230 ml of bromine (4.5 moles) is added at 20° C. to 26° C. over a period of 15 minutes. Hydrogen bromide gas is given off during the bromide addition, and a slurry of 3,5-dibromo-2,4,6-trimethylphenol is obtained. The temperature is increased to 70° C. to 75° C., and in the process, a solution is obtained. The solution is held at that temperature for 2 hours. The unreacted bromine is removed by distillation with the aid of 1 liter of carbon tetrachloride. When 1 liter of solvent remains with the product, the solution is cooled to 25° C. The light brown solid obtained is filtered and dried under a vacuum for 5 hours. A yield of 260 g is obtained, which analyzes by gas chromatography as 99% tribromomesitol.

(2) Hydrolysis of tribromomesitol to 3,5-dibromo-2,6-dimethyl-4-hydroxymethyl phenol The product of (B-1) above, 260 g, is dissolved in about 650 g of acetone at room temperature. About 520 g of water is added over a period of about 1.5 hours. The mixture is gradually heated to reflux (58° C.) over a period of about 1.5 hours. The reflux is maintained for an additional 1.5 hours. The white precipitate that forms is isolated by filtration at 25° C., and then vacuum dried at 60° C. The yield is 92.8%, and the product contains 87% of the desired product, 3,5-dibromo-4-hydroxymethyl-2,6-dimethyl phenol, and 13% 3,5-dibromo-2,6-dimethyl-4-hydroxymethyl phenyl ether by-product.

C. Preparation of Condensation Product of Dicyclopentadiene Phenol Resin and Meta Brominated Phenolic Compound In a reaction flask equipped with a mechanical stirrer, 330 grams (2 equiv.) of the dicyclopentadiene phenol resin from A above are melted at 130° C. To this are added 166.7 grams (0.5 equiv.) of the product from (B-2) above containing 3,5-dibromo-4-hydroxymethyl-2,6-dimethyl phenol. After stirring for about 1.5 hours at a temperature of 129° C. to 130° C., 160 grams of toluene are added. While maintaining the temperature at 113° C. to 119° C., the reaction mixture is stirred for about 6 hours, during which time the toluene/water azeotrope is removed overhead. The residual toluene and water are removed from the product by vacuum stripping on a rotoevaporator for about 1 hour at 140° C. at 8 to 9 mm Hg. The resulting product (I) has a Mettler softening point of 113.6° C.

D. Cyanation of Condensation Product from C

A Solution designated as A is prepared by dissolving 149.2 grams of cyanogen bromide in 800 ml of methylene chloride in a reaction flask at −10° C. A Solution designated as B is prepared by dissolving 227.3 g of the condensation product from C above and 135.2 grams of triethylamine in 350 ml of methylene chloride. While maintaining the temperature at between −10° C. and −22° C., Solution B is added dropwise to Solution A over a period of about 1.5 hours. Then an additional 6.2 grams of triethylamine is added over a period of about 2 minutes. The cooling is then removed and the reaction mixture allowed to digest while slowly warming to ambient temperature (about 23° C.) over a period of 1 hour. The reaction mixture is washed by extracting once with 400 ml of deionized water, twice with 100 ml of 0.2N HCl, and eight additional times with 300–400 ml portions of deionized water. The remaining organic phase is dried over MgSO$_4$ and filtered through filter paper. The reaction solvent is removed by vacuum stripping on a rotoevaporator. Two hundred grams of cyanated product having a calculated cyanate equivalent weight of about 210 is recovered.

E. Curing

The cyanated bromine-containing product from D above is blended with a halogen-free cyanated dicyclopentadiene phenol resin having an average functionality of about 2.27 and a calculated cyanate equivalent weight of about 190 so as to achieve a blended product containing 12% bromine by weight. The blending is conducted as follows:

Fifty-five grams of the halogen-free cyanated dicyclopentadiene phenol resin and 200 grams of the bromine-containing cyanated product from D above are melted and blended at about 130° C. To this blend is added 300 ppm by weight of cobalt as a 1% solution of Co(III) acetylacetonate in divinylbenzene. The catalyzed mixture is cured in a mold for 1 hour at 175° C., 2 hours at 225° C. and 1 hour at 240° C.

The above blended product designated as Sample A is subjected to testing to determine the properties thereof. The properties of the halogen-free cyanated dicyclopentadiene phenol resin cured with cobalt (III) acetylacetonate in divinylbenzene as described above is also determined for comparative purposes. This cured product is designated as sample B. The results are given in the following Table.

| PROPERTY | Sample A | Sample B* |
|---|---|---|
| $Tg^1$, °C. | 289 | 250 |
| Coefficient of Thermal Expansion$^2$, ppm/°C. | | |
| 70° C. | — | 52.4 |
| 80° C. | 49.9 | 50.3 |
| 90° C. | 57.9 | 53.2 |
| 100° C. | 53.9 | 53.6 |
| 110° C. | 54.7 | 53.1 |
| 120° C. | 52.9 | 52.8 |
| 130° C. | 50.8 | 51.5 |
| 140° C. | 53.4 | 55.1 |
| 150° C. | 57.7 | 52.2 |
| 160° C. | 55.9 | 55.6 |
| 170° C. | 60.2 | 56.9 |
| 180° C. | 54.4 | 59.3 |
| 190° C. | 56.8 | 59.0 |
| 200° C. | 62.1 | 64.9 |
| 210° C. | 61.6 | 67.8 |
| 220° C. | 60.1 | 57.9 |
| 230° C. | 61.0 | 66.7 |
| 240° C. | 63.9 | 79.2 |
| 250° C. | 55.0 | 89.0 |
| 260° C. | 60.2 | 156.0 |
| 270° C. | 67.1 | 165.0 |
| 280° C. | 73.4 | 150.0 |
| 290° C. | 86.6 | 158.0 |
| 300° C. | 82.9 | — |
| 310° C. | 61.5 | — |
| 320° C. | 81.8 | — |
| 330° C. | 109.0 | — |
| Thermal Decompositon$^3$ °C. | 394 | 410 |
| Dielectric Constant @ 21° C. | 3.07 | 2.91 |
| Dissipation Factor @ 21° C. | 0.00434 | 0.00287 |
| Moisture Pickup$^4$, % Wt. gain | 2.34 | 1.71 |
| Flame Retardancy$^5$, UL 94 rating | V-0 | No Rating |

FOOTNOTES TO TABLE
*Not an example of the present invention.
$^1$The glass transition temperature, Tg, is determined by Thermomechanical Analysis.
$^2$The coefficient of thermal expansion is a volumetric determination obtained by Thermomechanical Analysis and the results are parts per million by volume per degree centigrade.
$^3$The thermal decomposition temperature is determined by Thermogravimetric Analysis.
$^4$The moisture pickup test is conducted for 500 hours at 121° C. under 15 psig (103 kPa) steam pressure.
$^5$The flame retardancy rating is determined by the Underwriters Laboratory UL 94 Burn Test.

What is claimed is:
1. A hydrocarbon phenol cyanate resin represented by the following formula I

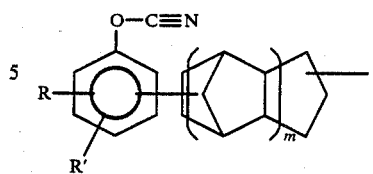
FORMULA I

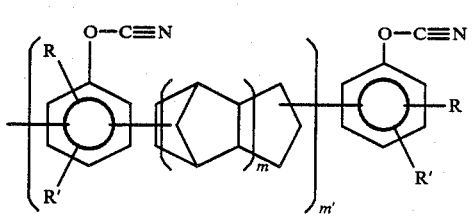

wherein each R is independently hydrogen or an alkyl group having from 1 to about 10 carbon atoms; each m independently has a value from 1 to about 6; m' has an average value from zero to about 4; each R' is independently hydrogen or a group represented by the following formula II

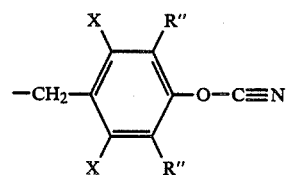
FORMULA II wherein each R" is independently an alkyl group having from 1 to about 4 carbon atoms; each X is a halogen; with the proviso that at least one R' group is a group represented by formula II.

2. A hydrocarbon phenol cyanate resin of claim 1 wherein each R is independently hydrogen or an alkyl group having from 1 to about 6 carbon atoms; each m independently has a value from 1 to about 3; and m' has an average a value from zero to about 2.

3. A hydrocarbon phenol cyanate resin of claim 1 wherein each R is independently hydrogen or an alkyl group having from 1 to about 2 carbon atoms; each X is bromine; each m independently has a value from 1 to about 2; and m' has a value from zero to about 1.

4. A hydrocarbon phenol cyanate resin of claim 3 wherein R is hydrogen, R" is methyl, and X is bromine.

5. A hydrocarbon phenol cyanate resin mixture comprising
(A) at least one hydrocarbon phenol cyanate resin represented by the following formula I

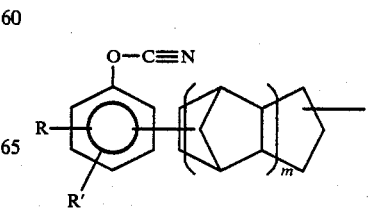
FORMULA I

-continued

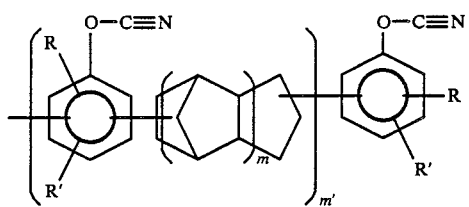

wherein each R is independently hydrogen or an alkyl group having from 1 to about 10 carbon atoms; each m independently has a value from 1 to about 6; each m' has an average value from zero to about 4; each R' is independently hydrogen or a group represented by the following formula II;

FORMULA II

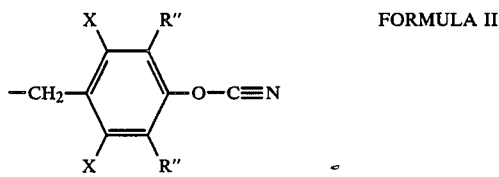

wherein each R" is independently an alkyl group having from 1 to about 4 carbon atoms; each X is a halogen; with the proviso that at least one R' group is a group represented by formula II; and (B) at least one halogen-free hydrocarbon phenol cyanate resin represented by the following formula III

FORMULA III

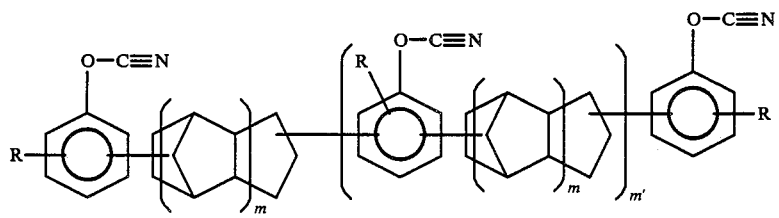

wherein each R is independently hydrogen or an alkyl group having from 1 to about 10 carbon atoms; each m independently has a value from 1 to about 6; m' has an average value from zero to about 4; and wherein component (A) is present in an amount of from about 1 to about 99 percent by weight and component (B) is present in an amount of from about 99 to about 1 percent by weight based upon the combined weight of components (A) and (B).

6. A hydrocarbon phenol cyanate resin mixture of claim 5 wherein components (A) and (B) are employed in an amount of from about 10 to about 90 percent by weight of component (A) and from about 90 to about 10 percent by weight of component (B) based upon the combined weight of components (A) and (B); each R is independently hydrogen or an alkyl group having from 1 to about 6 carbon atoms; each m independently has a value from about 1 to about 3; and m' has an average value from about zero to about 2.

7. A hydrocarbon phenol cyanate resin mixture of claim 5 wherein components (A) and (B) are employed in an amount of from about 15 to about 85 percent by weight of component (A) and from about 85 to about 15 percent by weight of component (B) based upon the combined weight of components (A) and (B); each R is independently hydrogen or an alkyl group having from 1 to about 2 carbon atoms; each X is bromine; each m independently has a value from about 1 to about 2; and m' has an average value from about zero to about 1.

8. A hydrocarbon phenol cyanate resin of claim 7 wherein in components (A) and (B) R is hydrogen, R" is methyl and X is bromine.

9. A curable composition comprising a hydrocarbon phenol cyanate resin of claim 1 with a curing quality of a suitable curing agent or catalyst.

10. The curable composition of claim 9 wherein said curing agent or catalyst is a base, acid, salt, nitrogen or phosphorous compound, transition metal salt or complex, or a combination thereof.

11. The curable composition of claim 10 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

12. A curable composition comprising a hydrocarbon phenol cyanate resin of claim 2 with a curing quantity of a suitable curing agent or catalyst.

13. The curable composition of claim 12 wherein said curing agent or catalyst is a base, acid, salt, nitrogen or phosphorous compound, transition metal salt or complex, or a combination thereof.

14. The curable composition of claim 13 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

15. A curable composition comprising a hydrocarbon phenol cyanate resin of claim 3 with a curing quantity of a suitable curing agent or catalyst.

16. The curable composition of claim 15 wherein said curing agent or catalyst is a base, acid salt, nitrogen or phosphorous compound, transition metal salt or complex, or a combination thereof.

17. The curable composition of claim 16 wherein said curing agent or catalyst is cobalt octoate, cobalt naphthenate, cobat acetylacetonate, zinc octoate, zinc naphthenate, tin octoate, diazobicyclo-(2,2,2)-octane, triethylamine, an alkyl phenol or a combination thereof.

18. A curable composition comprising a hydrocarbon phenol cyanate resin of claim 4 with a curing quantity of a suitable curing agent or catalyst.

19. The curable composition of claim 18 wherein said curing agent or catalyst is a base, acid, salt, nitrogen or phosphorous compound, transition metal salt or complex, or a combination thereof.

20. The curable composition of claim 19 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

21. A curable composition comprising a hydrocarbon phenol cyanate resin of claim 5 with a curing quantity of a suitable curing agent or catalyst.

22. The curable composition of claim 21 wherein said curing agent or catalyst is a base, acid, salt, nitrogen or phosphorous compound, transition metal salt or complex, or a combination thereof.

23. The curable composition of claim 22 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

24. A curable composition comprising a hydrocarbon phenol cyanate resin of claim 6 with a curing quantity of a suitable curing agent or catalyst.

25. The curable composition of claim 24 wherein said curing agent or catalyst is a base, acid, salt, nitrogen or phosphorous compound, transition metal salt or complex, or a combination thereof.

26. The curable composition of claim 25 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

27. A curable composition comprising a hydrocarbon phenol cyanate resin of claim 7 with a curing quantity of a suitable curing agent or catalyst.

28. The curable composition of claim 27 wherein said curing agent or catalyst is a base, acid, salt, nitrogen or phosphorous compound, transition metal salt or complex, or a combination thereof.

29. The curable composition of claim 28 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

30. A curable composition comprising a hydrocarbon phenol cyanate resin of claim 8 with a curing quantity of a suitable curing agent or catalyst.

31. The curable composition of claim 30 wherein said curing agent or catalyst is a base, acid, salt, nitrogen or phosphorous compound, transition metal salt or complex, or a combination thereof.

32. The curable composition of claim 31 wherein said curing agent or catalyst is cobalt octoate, cobalt naphthenate, cobalt acetylacetonate, zinc octoate, zinc naphthenate, tin octoate, diazobicyclo-(2,2,2)-octane, triethylamine, an alkyl phenol or a combination thereof.

33. The product resulting from curing the composition of claim 9.

34. The product resulting from curing the composition of claim 10.

35. The product resulting from curing the composition of claim 11.

36. The product resulting from curing the composition of claim 12.

37. The product resulting from curing the composition of claim 13.

38. The product resulting from curing the composition of claim 14.

39. The product resulting from curing the composition of claim 15.

40. The product resulting from curing the composition of claim 16.

41. The product resulting from curing the composition of claim 17.

42. The product resulting from curing the composition of claim 18.

43. The product resulting from curing the composition of claim 19.

44. The product resulting from curing the composition of claim 20.

45. The product resulting from curing the composition of claim 21.

46. The product resulting from curing the composition of claim 22.

47. The product resulting from curing the composition of claim 23.

48. The product resulting from curing the composition of claim 24.

49. The product resulting from curing the composition of claim 25.

50. The product resulting from curing the composition of claim 26.

51. The product resulting from curing the composition of claim 27.

52. The product resulting from curing the composition of claim 28.

53. The product resulting from curing the composition of claim 29.

54. The product resulting from curing the composition of claim 30.

55. The product resulting from curing the composition of claim 31.

56. The product resulting from curing the composition of claim 32.

* * * * *